US012700479B2

(12) United States Patent
    Hanaoka

(10) Patent No.: US 12,700,479 B2
(45) Date of Patent: Aug. 4, 2026

(54) INFORMATION PROCESSING SYSTEM, INFORMATION PROCESSING METHOD, AND STORAGE MEDIUM

(71) Applicant: Resonac Corporation, Tokyo (JP)

(72) Inventor: Kyohei Hanaoka, Tokyo (JP)

( * ) Notice: Subject to any disclaimer, the term of this patent is extended or adjusted under 35 U.S.C. 154(b) by 407 days.

(21) Appl. No.: 18/254,384

(22) PCT Filed: Nov. 22, 2021

(86) PCT No.: PCT/JP2021/042833
    § 371 (c)(1),
    (2) Date: May 25, 2023

(87) PCT Pub. No.: WO2022/113945
    PCT Pub. Date: Jun. 2, 2022

(65) Prior Publication Data
    US 2024/0047018 A1     Feb. 8, 2024

(30) Foreign Application Priority Data

Nov. 27, 2020   (JP) ................................. 2020-197046

(51) Int. Cl.
    G16C 20/30        (2019.01)
    G06N 3/044        (2023.01)
    (Continued)
(52) U.S. Cl.
    CPC ............. G16C 20/30 (2019.02); G16C 20/70 (2019.02); *G06N 3/044* (2023.01); *G06N 3/0464* (2023.01);
    (Continued)
(58) Field of Classification Search
    CPC ........ G16C 20/30; G16C 20/70; G16C 60/00; G06N 3/044; G06N 3/0464; G06N 3/08; G06N 20/00
    See application file for complete search history.

(56) References Cited

U.S. PATENT DOCUMENTS

| | | | |
|---|---|---|---|
| 2014/0163937 A1 | 6/2014 | Lee | |
| 2018/0360313 A1* | 12/2018 | Zhang | ..................... G06T 7/337 |
| 2021/0073671 A1* | 3/2021 | Puri | ......................... G06N 5/04 |

FOREIGN PATENT DOCUMENTS

| | | |
|---|---|---|
| JP | 2019-028879 | 2/2019 |
| JP | 2020-030638 | 2/2020 |

(Continued)

OTHER PUBLICATIONS

Brown et al. (General Blending Models for Data From Mixture Experiments. Technometrics. Oct. 2, 2015;57(4):449-456. doi: 10.1080/ 00401706.2014.947003. Epub Nov. 16, 2015. PMID: 26681812; PMCID: PMC4673519.) (Year: 2015).*

(Continued)

*Primary Examiner* — Christian T Bryant
(74) *Attorney, Agent, or Firm* — SHIPWAY IP

(57)           ABSTRACT

An information processing system according to an embodiment includes at least one processor. The at least one processor is configured to acquire a numerical representation and a combination ratio for each of a plurality of component objects, execute machine learning based on a plurality of the numerical representations to calculate a plurality of regression parameters corresponding to the plurality of component objects, and apply a plurality of the combination ratios to a regression model defined by the plurality of regression parameters to calculate a predicted value indicating characteristics of a composite object obtained by combining plurality of component objects.

7 Claims, 5 Drawing Sheets

(51) Int. Cl.

| | |
|---|---|
| *G06N 3/0464* | (2023.01) |
| *G06N 3/08* | (2023.01) |
| *G06N 20/00* | (2019.01) |
| *G16C 20/70* | (2019.01) |
| *G16C 60/00* | (2019.01) |

(52) U.S. Cl.
CPC .............. *G06N 3/08* (2013.01); *G06N 20/00* (2019.01); *G16C 60/00* (2019.02)

(56)                    References Cited

FOREIGN PATENT DOCUMENTS

| | | |
|---|---|---|
| JP | 2020-038493 | 3/2020 |
| JP | 2020-038495 | 3/2020 |
| JP | 2020-161044 | 10/2020 |
| WO | 2020/090805 | 5/2020 |

OTHER PUBLICATIONS

International Preliminary Report on Patentability with Written Opinion dated Jun. 8, 2023 for PCT/JP2021/042833.

International Search Report dated Mar. 1, 2022 for PCT/JP2021/042833.

Claudius K et al., "Simplex Lattice Method: A Predictive Tool for Concrete Materials", Americal Journal of Engineering Research (AJER), vol. 6, No. 4, Apr. 1, 2017, p. 19-p. 27.

Raffaele Vitale et al., "Kernel-Partial Least Squares regression coupled to pseudo-sample trajectories for the analysis of mixture designs of experiments", Chemometrics and Intelligent Laboratory Systems, vol. 175, Feb. 13, 2018, p. 37-p. 46.

Extended Search Report in corresponding European Application No. 21897918.5, dated Apr. 16, 2024.

* cited by examiner

*Fig.3*

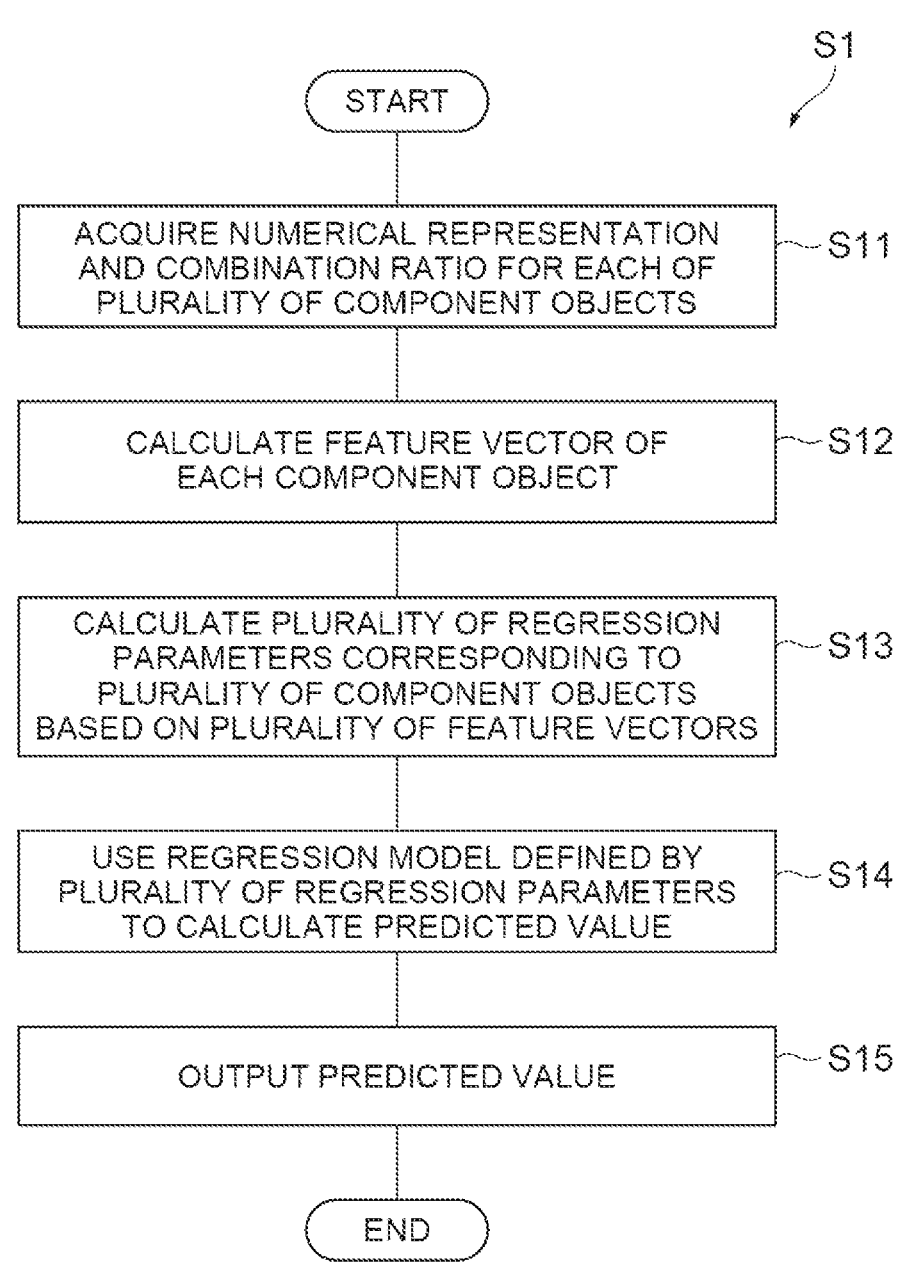

S1

START

ACQUIRE NUMERICAL REPRESENTATION
AND COMBINATION RATIO FOR EACH OF
PLURALITY OF COMPONENT OBJECTS — S11

CALCULATE FEATURE VECTOR OF
EACH COMPONENT OBJECT — S12

CALCULATE PLURALITY OF REGRESSION
PARAMETERS CORRESPONDING TO
PLURALITY OF COMPONENT OBJECTS
BASED ON PLURALITY OF FEATURE VECTORS — S13

USE REGRESSION MODEL DEFINED BY
PLURALITY OF REGRESSION PARAMETERS
TO CALCULATE PREDICTED VALUE — S14

OUTPUT PREDICTED VALUE — S15

END

1

INFORMATION PROCESSING SYSTEM, INFORMATION PROCESSING METHOD, AND STORAGE MEDIUM

CROSS-REFERENCE TO RELATED APPLICATIONS

This application is a 35 U.S.C. § 371 national phase application of PCT/JP2021/042833, filed on Nov. 22, 2021, which claims priority to Japanese Patent Application No. 2020-197046, filed on Nov. 27, 2020.

TECHNICAL FIELD

One aspect of the present disclosure relates to an information processing system, an information processing method, and an information processing program.

BACKGROUND ART

A method of analyzing a composite object obtained by combining a plurality of component objects using machine learning has been used. For example, Patent Literature 1 describes a method of predicting the bondability between the three-dimensional structure of a biopolymer and the three-dimensional structure of a compound. This method includes: generating a predicted three-dimensional structure of a complex of a biopolymer and a compound based on the three-dimensional structure of the biopolymer and the three-dimensional structure of the compound; converting the predicted three-dimensional structure into a predicted three-dimensional structure vector representing a result of comparison with an interaction pattern; and predicting the bondability between the three-dimensional structure of the biopolymer and the three-dimensional structure of the compound by determining the predicted three-dimensional structure vector using a machine learning algorithm.

CITATION LIST

Patent Literature

Patent Literature 1: JP 2019-28879 A

SUMMARY OF INVENTION

Technical Problem

When there are various or many component objects, it is not possible to prepare a sufficient amount of data for these component objects. As a result, the accuracy of analysis of a composite object may not reach the expected level. Therefore, there has been a demand for a mechanism for improving the accuracy of analysis of a composite object even in a case where a sufficient amount of data cannot be prepared for component objects.

Solution to Problem

An information processing system according to one aspect of the present disclosure includes at least one processor. The at least one processor is configured to: acquire a numerical representation and a combination ratio for each of a plurality of component objects; execute machine learning based on a plurality of the numerical representations to calculate a plurality of regression parameters corresponding to the plurality of component objects; and apply a plurality of the combination ratios to a regression model defined by the plurality of regression parameters to calculate a predicted value indicating characteristics of a composite object obtained by combining plurality of component objects.

An information processing method according to one aspect of the present disclosure is executed by an information processing system comprising at least one processor. The information processing method includes: acquiring a numerical representation and a combination ratio for each of a plurality of component objects; executing machine learning based on a plurality of the numerical representations to calculate a plurality of regression parameters corresponding to the plurality of component objects; and applying a plurality of the combination ratios to a regression model defined by the plurality of regression parameters to calculate a predicted value indicating characteristics of a composite object obtained by combining plurality of component objects.

An information processing program according to one aspect of the present disclosure causes a computer to execute: acquiring a numerical representation and a combination ratio for each of a plurality of component objects; executing machine learning based on a plurality of the numerical representations to calculate a plurality of regression parameters corresponding to the plurality of component objects; and applying a plurality of the combination ratios to a regression model defined by the plurality of regression parameters to calculate a predicted value indicating characteristics of a composite object obtained by combining plurality of component objects.

In such aspects, the machine learning is performed based on the data of each component object, and the plurality of regression parameters corresponding to the plurality of component objects are calculated. Then, the combination ratio is applied to the regression model defined by the regression parameters to predict the characteristics of the composite object. By utilizing the machine learning and regression model, it is possible to improve the accuracy of analysis of composite object even in a case where a sufficient amount of data cannot be prepared for the component objects.

Advantageous Effects of Invention

According to one aspect of the present disclosure, it is possible to improve the accuracy of analysis of composite object even in a case where a sufficient amount of data cannot be prepared for the component objects.

BRIEF DESCRIPTION OF DRAWINGS

FIG. 3 is a flowchart showing an example of an operation of the information processing system according to the embodiment.

DESCRIPTION OF EMBODIMENTS

Figure 1:
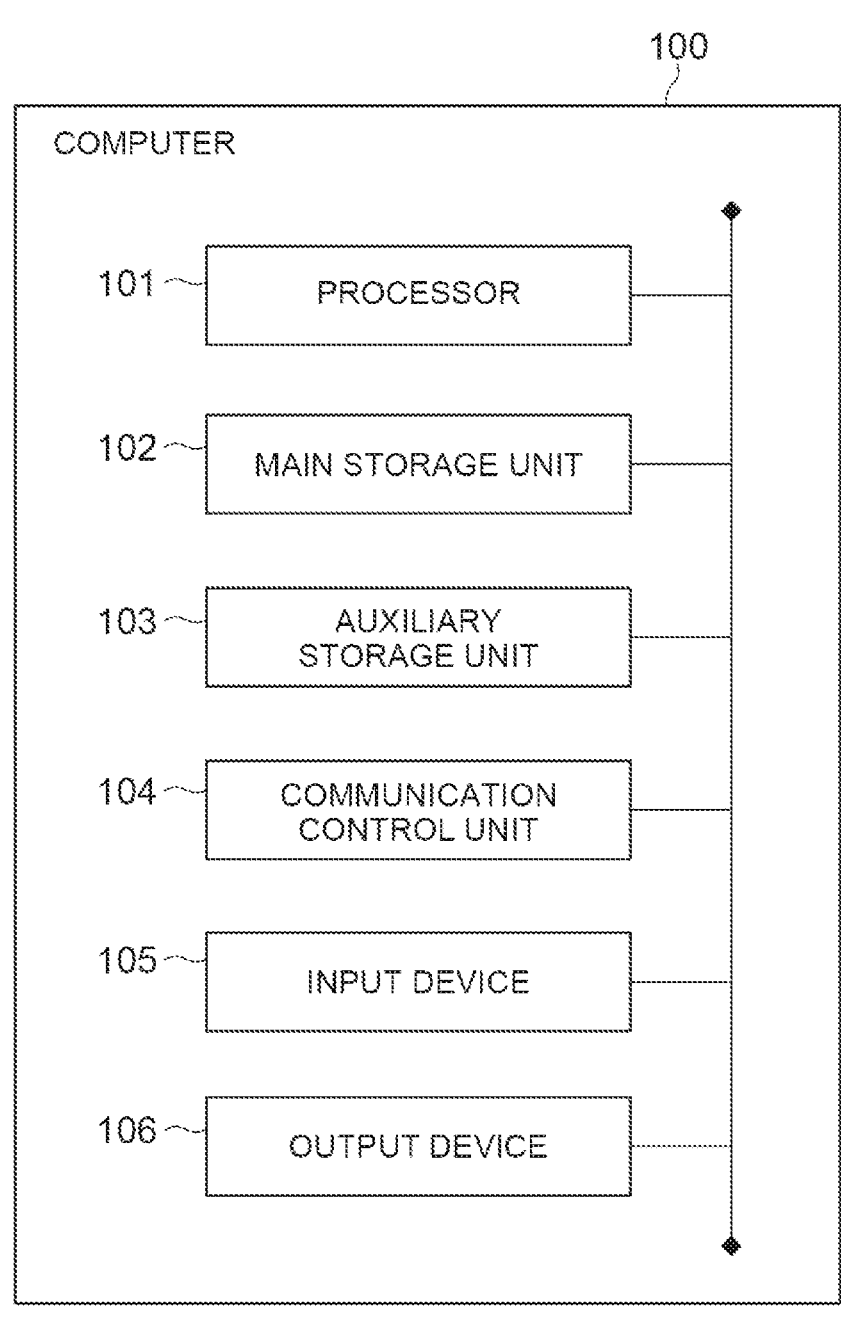
FIG. 1 is a diagram showing an example of the hardware configuration of a computer configuring an information processing system according to an embodiment.

Hereinafter, an embodiment in the present disclosure will be described in detail with reference to the accompanying diagrams. In addition, in the description of the diagrams, the same or equivalent elements are denoted by the same reference numerals, and the repeated description thereof will be omitted.

[System Overview]

An information processing system 10 according to the embodiment is a computer system that performs an analysis on a composite object obtained by combining a plurality of component objects at a predetermined combination ratio. A component object refers to a tangible object or an intangible object used to generate a composite object. The composite object can be a tangible object or an intangible object. Examples of a tangible object include any substance or object. Examples of an intangible object include data and information. "Combining a plurality of component objects" refers to a process of making a plurality of component objects into one object, that is, a composite object. The method of combining is not limited, and may be, for example, compounding, blending, synthesis, bonding, mixing, merging, combination, chemical combination, or uniting, or other methods. The analysis of a composite object refers to a process for obtaining data indicating a certain feature of the composite object.

The plurality of component objects may be any plurality of types of materials. In this case, the composite object is a multi-component substance produced by these materials. The materials are arbitrary components used to produce a multi-component substance. For example, the plurality of materials may be any plurality of types of molecules or atoms. In this case, the composite object is a multi-component substance obtained by combining these molecules or atoms using an arbitrary method. For example, the material may be a polymer or monomer and correspondingly the multi-component substance may be a polymer alloy. The material may be a monomer and correspondingly the multi-component substance may be a polymer. The material may be a medicinal substance, that is, a chemical substance having a pharmacological action, and correspondingly, the multi-component substance may be a medicine.

The information processing system 10 performs machine learning for the analysis of a composite object. The machine learning is a method of learning based on given information to autonomously find a law or rule. The specific method of machine learning is not limited. For example, the information processing system 10 may perform machine learning using a machine learning model that is a calculation model configured to include a neural network. The neural network is an information processing model that imitates the mechanism of the human cranial nerve system. As a more specific example, the information processing system 10 may perform machine learning by using at least one of graph neural network (GNN), convolutional neural network (CNN), recurrent neural network (RNN), attention RNN, and multi-head attention.

[System Configuration]

The information processing system 10 is configured to include one or more computers. In a case where a plurality of computers are used, one information processing system 10 is logically constructed by connecting these computers to each other through a communication network, such as the Internet or an intranet.

FIG. 1 is a diagram showing an example of a general hardware configuration of a computer 100 configuring the information processing system 10. For example, the computer 100 includes a processor 101, such as a CPU, for executing an operating system, an application program, and the like, a main storage unit 102 configured by a ROM and a RAM, an auxiliary storage unit 103 configured by a hard disk, a flash memory, and the like, a communication control unit 104 configured by a network card or a wireless communication module, an input device 105 such as a keyboard and a mouse, and an output device 106 such as a monitor.

Each functional element of the information processing system 10 is realized by reading a predetermined program on the processor 101 or the main storage unit 102 and causing the processor 101 to execute the program. The processor 101 operates the communication control unit 104, the input device 105, or the output device 106 according to the program and performs reading and writing of data in the main storage unit 102 or the auxiliary storage unit 103. The data or database required for the processing is stored in the main storage unit 102 or the auxiliary storage unit 103.

Figure 2:
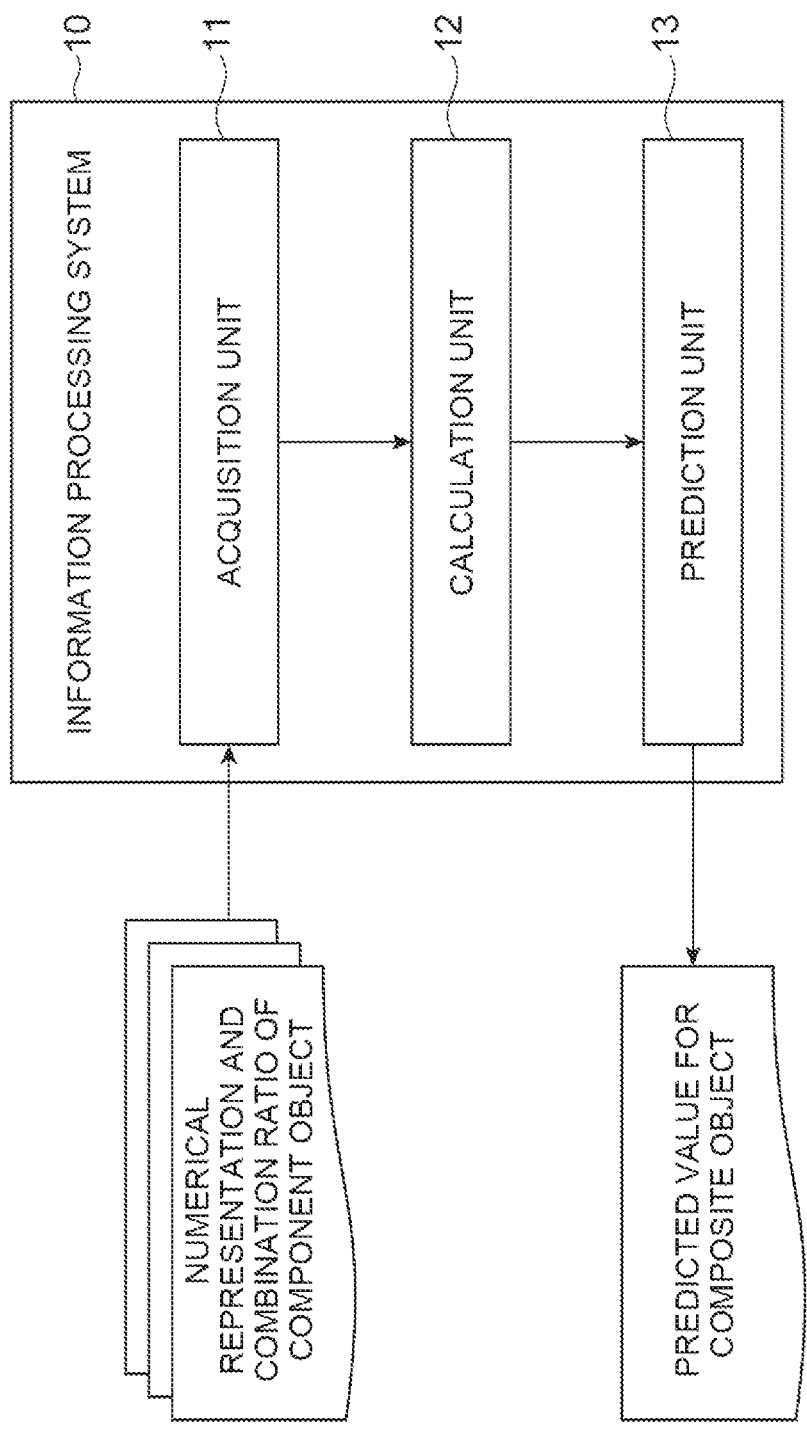
FIG. 2 is a diagram showing an example of the functional configuration of the information processing system according to the embodiment.

FIG. 2 is a diagram showing an example of the functional configuration of the information processing system 10. The information processing system 10 includes an acquisition unit 11, a calculation unit 12, and a prediction unit 13 as functional elements.

The acquisition unit 11 is a functional element that acquires data related to a plurality of component objects. Specifically, the acquisition unit 11 acquires a numerical representation and a combination ratio for each of the plurality of component objects. The numerical representation of the component object refers to data representing arbitrary attributes of the component object using a plurality of numerical values. The attribute of the component object refers to a property or characteristic of the component object. The numerical representation may be visualized by various methods. For example, the numerical representation may be visualized by a method such as a number, an alphabetic character, a text, a molecular graph, a vector, an image, or time-series data, or may be visualized by a combination of any two or more of these methods. The individual numerical values constituting the numerical representation may be represented in decimal or another notational system such as binary, hexadecimal, etc. The combination ratio of component objects refers to a ratio among a plurality of component objects. A specific type, unit, and expression method of the combination ratio are not limited and may be arbitrarily determined according to the component object or the composite object. For example, the combination ratio may be represented by a ratio such as a percentage, may be represented by a histogram, or may be represented by an absolute amount of each component object.

The calculation unit 12 is a functional element that calculates a regression parameter of a regression model for predicting characteristics of the composite object. Specifically, the calculation unit 12 executes machine learning based on the plurality of numerical representations corresponding to the plurality of component objects to calculate the regression parameter. The regression model refers to an expression for obtaining one or more values of one or more objective variables y when one or more values of one or more explanatory variables x are given. The regression model may be a linear regression model or a non-linear regression model. Examples of the regression model may include the Scheffe polynomial. The regression model may however be another parametric model. The regression parameter refers to a numerical value included in the regression model.

The prediction unit 13 is a functional element that predicts characteristics of the composite object and outputs a predicted value. The characteristics of the composite object refer to characteristics unique to the composite object.

Specifically, the prediction unit 13 applies the combination ratio to the regression model defined by the calculated regression parameter to calculate the predicted value. In other words, the prediction unit 13 substitutes a plurality of the combination ratios into the regression model to calculate the predicted value.

In one example, a combination of the calculation unit 12 and the prediction unit 13 is implemented by one machine learning model. Alternatively, the calculation unit 12 may be implemented by a machine learning model, and the prediction unit 13 may be implemented by an algorithm that does not use a machine learning model.

In one example, each of at least one machine learning model used in the present embodiment is a learned model that is expected to have the highest estimation accuracy, and thus may be referred to as a "best machine learning model". However, it should be noted that the learned model is not always "best in reality". The learned model is generated by a given computer processing training data including a large number of combinations of input vectors and labels. The given computer inputs the input vector to a machine learning model to calculate an output value, and calculates an error between the output value and the label indicated by training data. The output value is, for example, the predicted value. The error between the output value and the label may be a difference between the prediction result and the ground truth. The computer updates given parameters in the machine learning model based on the error. The computer generates the learned model by repeating such learning. The computer that generates the learned model is not limited, and may be, for example, the information processing system 10 or another computer system. Processing that generates the learned model may be referred to as a learning phase, and processing that uses the learned model may be referred to as an operation phase.

In one example, the whole of the machine learning model used in the present embodiment may be described by a function that does not depend on an input order. This mechanism makes it possible to eliminate an influence of an arrangement order of a plurality of vectors in the machine learning.

[System Operation]

With reference to FIG. 3, the operation of the information processing system 10 and the information processing method according to the present embodiment will be described. FIG. 3 is a flowchart showing an example of the operation of the information processing system 10 as a processing flow S1. The processing flow S1 corresponds to the operation phase.

In step S11, the acquisition unit 11 acquires a numerical representation and a combination ratio for each of a plurality of component objects. As an example, if information on two component objects Ea and Eb is input, the acquisition unit 11 acquires, for example, a numerical representation {1, 1, 2, 3, 4, 3, 3, 5, 6, 7, 5, 4} of the component object Ea, a numerical representation {1, 1, 5, 6, 4, 3, 3, 5, 1, 7, 0, 0} of the component object Eb, and a combination ratio {0.7, 0.3} of the component object Ea and Eb. In this example, each numerical representation is represented by a vector. The combination ratio {0.7, 0.3} means that a composite object is obtained by using the component objects Ea and Eb at a ratio of 7:3.

The acquisition unit 11 may acquire the data of each of the plurality of component objects by using any method. For example, the acquisition unit 11 may access a given database to read the data, or may receive the data from another computer or computer system, or may receive the data input by the user of the information processing system 10. Alternatively, the acquisition unit 11 may acquire data by any two or more of these methods.

In step S12, the calculation unit 12 calculates a feature vector based on a numerical representation for each of the plurality of component objects. The feature vector refers to a vector indicating a feature of the component object. The feature of the component object refers to any element that makes the component object different from other objects. The vector refers to an n-dimensional quantity having n numerical values, and may be expressed as a one-dimensional array.

In step S13, the calculation unit 12 calculates a plurality of regression parameters corresponding to the plurality of component objects based on the calculated plurality of feature vectors.

In step S14, the prediction unit 13 uses a regression model defined by the calculated plurality of regression parameters to calculate a predicted value indicating characteristics of a composite object. The regression model defined by the regression parameter is a regression model in which a specific numerical value is determined as the regression parameter. The prediction unit 13 applies the plurality of combination ratios to the regression model to calculate the predicted value.

In step S15, the prediction unit 13 outputs the predicted value. A method of outputting the predicted value is not limited. For example, the prediction unit 13 may store the predicted value in a given database, send the predicted value to another computer or computer system, or display the predicted value on a display device. Alternatively, the prediction unit 13 may output the predicted value to another functional element for subsequent processing in the information processing system 10.

Figure 4:
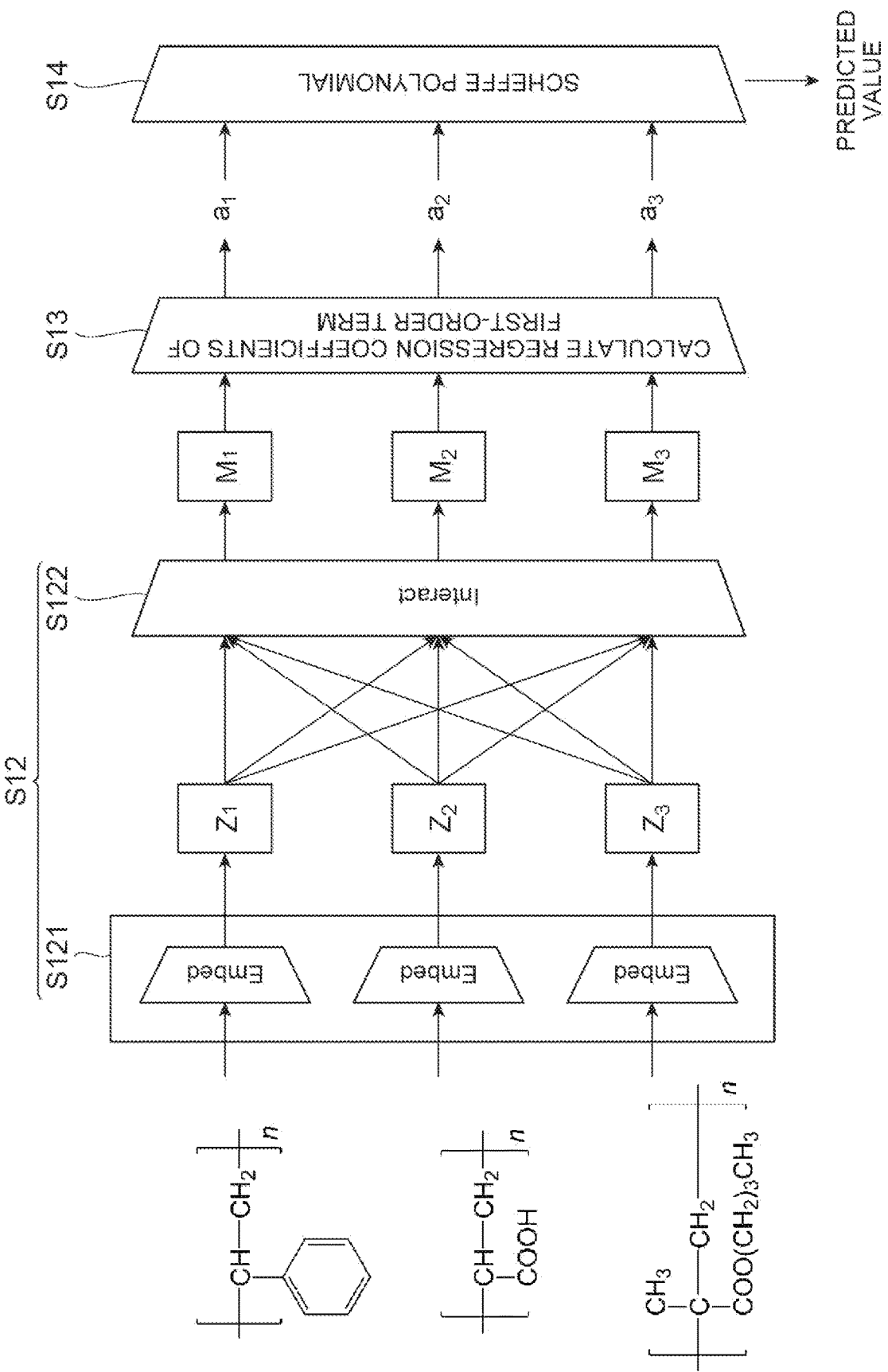
FIG. 4 is a diagram showing an example of a procedure for calculating a regression parameter.
Figure 5:
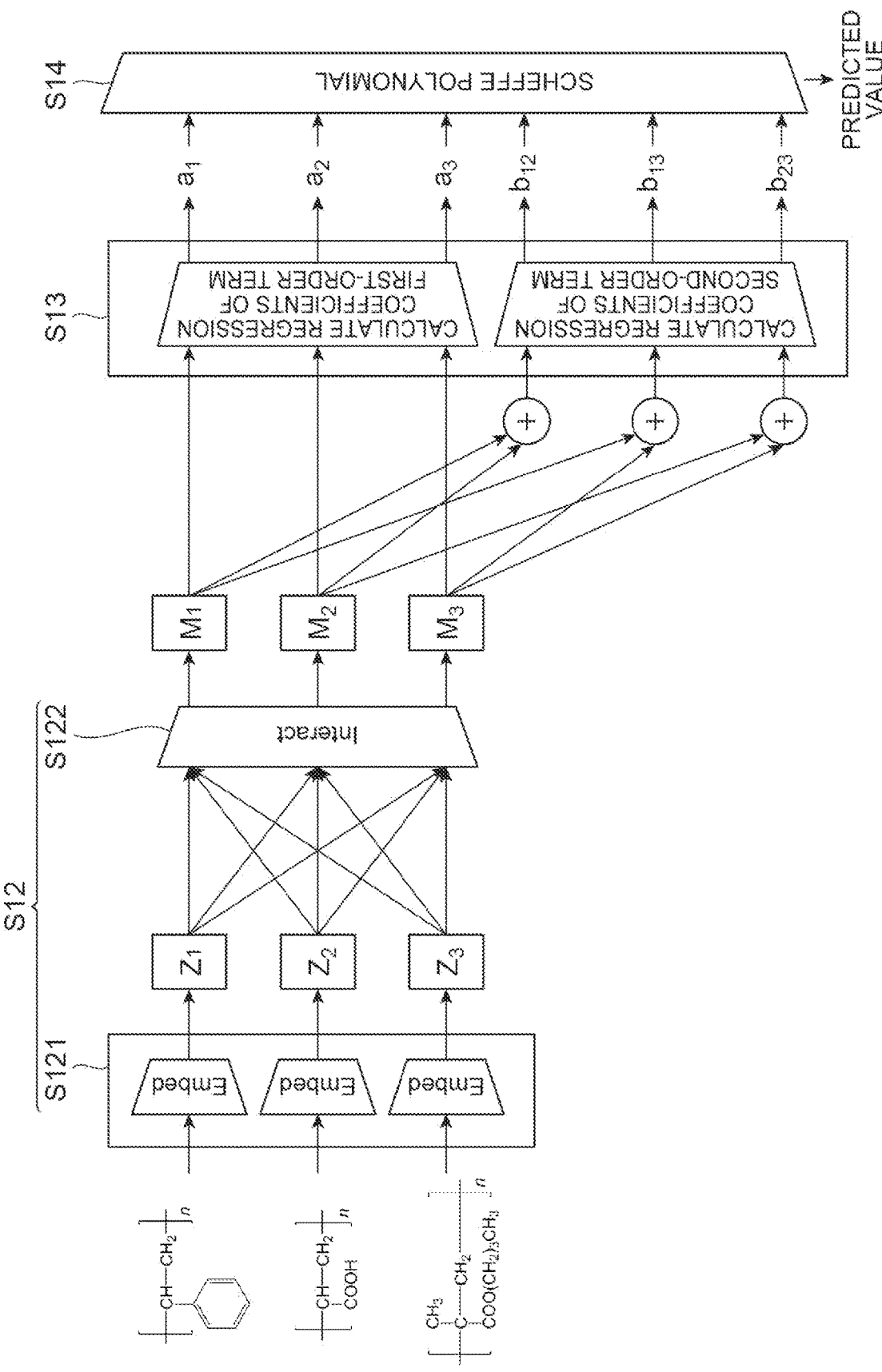
FIG. 5 is a diagram showing another example of a procedure for calculating a regression parameter.

With reference to FIGS. 4 and 5, a process related to the regression model will be described in more detail. FIGS. 4 and 5 are diagrams showing examples of a procedure for calculating the regression parameters. In any example, the component object indicates three types of materials (polymers): polystyrene, polyacrylic acid, and poly(butyl methacrylate). Any form of numerical representation may be provided for each of these materials.

The above-mentioned Scheffe polynomial is often used in issues related to the blending of materials. Therefore, in the examples of FIGS. 4 and 5, it is assumed that the regression model is the Scheffe polynomial.

The example of FIG. 4 will be described. In step S121 that is part of step S12, the calculation unit 12 calculates a feature vector Z from the numerical representation for each of the plurality of component objects by a machine learning model for an embedding function for calculating features of the vector. This machine learning model is a learned model. In the embedding function, an input vector and an output vector have a one to-one relationship. In this example, the input vector is the numerical representation and the output vector is the feature vector Z. The calculation unit 12 inputs the plurality of numerical representations corresponding to the plurality of component objects into the model for the embedding function to calculate the feature vector Z of each of the plurality of component objects. In one example, for each of the plurality of component objects, the calculation unit 12 inputs the numerical representation corresponding to the component object into the model for the embedding function to calculate the feature vector Z of the component object. In one example, the model for the embedding function may generate the feature vector Z that is a fixed-length vector from the numerical representation that is unstructured data.

The unstructured data refers to data that is not represented by a fixed-length vector. In the example of FIG. 4, the calculation unit 12 calculates a feature vector $Z_1$ corresponding to polystyrene, a feature vector $Z_2$ corresponding to polyacrylic acid, and a feature vector $Z_3$ corresponding to poly(butyl methacrylate).

The machine learning model for the embedding function is not limited, and may be determined by an arbitrary policy in consideration of factors such as types of the component object and the composite object. For example, the calculation unit 12 may execute the embedding function using graph neural network (GNN), convolutional neural network (CNN), or recursive neural network (RNN).

In step S122 that is part of step S12, the calculation unit 12 calculates another feature vector M from the feature vector Z for the plurality of component objects by a machine learning model for an interaction function for interacting a plurality of vectors. This machine learning model is a learned model. In the interaction function, an input vector and an output vector have a one to-one relationship. In this example, the input vector is the feature vector Z and the output vector is the feature vector M. In one example, the calculation unit 12 inputs a set of the plurality of feature vectors Z corresponding to the plurality of component objects into a model for the interaction function to calculate the feature vector M for each of the plurality of component objects. In the example of FIG. 4, the calculation unit 12 calculates a feature vector $M_1$ corresponding to polystyrene, a feature vector $M_2$ corresponding to polyacrylic acid, and a feature vector $M_3$ corresponding to poly(butyl methacrylate).

The machine learning model for the interaction function is not limited, and may be determined by an arbitrary policy in consideration of factors such as types of the component object and the composite object. For example, the calculation unit 12 may use Attention RNN or a Multi-Head Attention to execute the machine learning for the interaction function. In another example, the calculation unit 12 may calculate the feature vector M by an interaction function that does not include a learning parameter.

In step S13 shown in FIG. 4, the calculation unit 12 calculates a regression parameter a of a first-order term of a linear regression model from the feature vector M, for each of a plurality of component objects. In one example, the calculation unit 12 calculates the regression parameter by a machine learning model. This machine learning model is a learned model. In a function for calculating the regression parameter of the first-order term, an input vector and an output value have a one to-one relationship. In this example, the input vector is the feature vector M, and the output value is the regression parameter a. In one example, the calculation unit 12 inputs a set of the plurality of feature vectors M corresponding to the plurality of component objects into the machine learning model to calculate the regression parameter a for each of the plurality of component objects. In the example of FIG. 4, the calculation unit 12 calculates a regression parameter $a_1$ corresponding to polystyrene, a regression parameter $a_2$ corresponding to polyacrylic acid, and a regression parameter $a_3$ corresponding to poly(butyl methacrylate).

The machine learning model for calculating the regression parameter is not limited, and may be determined in an arbitrary policy in consideration of factors such as types of the component object and the composite object. For example, the calculation unit 12 may use a fully connected neural network (FCNN) to calculate the regression parameter.

In step S14 shown in FIG. 4, the prediction unit 13 calculates a predicted value E by the following Scheffe polynomial (1) defined by three the regression parameters $a_1$, $a_2$, and $a_3$. The regression parameter a may be said to be a regression coefficient of the first-order term of the equation (1). The predicted value E indicates characteristics of a multi-component substance (polymer alloy) obtained from polystyrene, polyacrylic acid, and poly(butyl methacrylate). A variable r in the equation (1) means the combination ratio. The combination ratios of polystyrene, polyacrylic acid, and poly(butyl methacrylate) are represented by $r_1$, $r_2$, and $r_3$, respectively.

[Equation 1]

$$E = \sum_{1 \le i \le 3} a_i r_i \tag{1}$$

An example of FIG. 5 will be described. In the example of FIG. 5, step S12 including steps S121 and S122 is the same as the example of FIG. 4, and steps S13 and S14 are different from the example of FIG. 4.

In step S13 illustrated in FIG. 5, the calculation unit 12 calculates a regression parameter of a linear regression model from the feature vector M, for each of the plurality of component objects. Specifically, the calculation unit 12 calculates a regression parameter a of a first-order term and a regression parameter b of a second-order term. In one example, the calculation unit 12 calculates the regression parameter by machine learning such as FCNN. The machine learning model is prepared for each of the first-order term and the second-order term of the linear regression model.

As in the example of FIG. 4, in a function for calculating the regression parameter of the first-order term, an input vector and an output value have a one to-one relationship. In this example, the input vector is the feature vector M, and the output value is the regression parameter a. In one example, the calculation unit 12 inputs a set of the plurality of feature vectors M corresponding to the plurality of component objects into the machine learning model to calculate the regression parameter a for each of the plurality of component objects. Also in the example of FIG. 5, the calculation unit 12 calculates a regression parameter $a_1$ corresponding to polystyrene, a regression parameter $a_2$ corresponding to polyacrylic acid, and a regression parameter $a_3$ corresponding to poly(butyl methacrylate).

In a function for calculating the regression parameter of the second-order term, each input vector is obtained by combining two feature vectors. This function is a function that calculates one regression parameter from two vectors. In this example, two feature vectors M are synthesized. In the example of FIG. 5, the calculation unit 12 synthesizes two feature vectors $M_1$ and $M_2$ to generate a first input vector, synthesizes two feature vectors $M_1$ and $M_3$ to generate a second input vector, and synthesizes two feature vectors $M_2$ and $M_3$ to generate a third input vector. Therefore, the first input vector corresponds to polystyrene and polyacrylic acid, the second input vector corresponds to polystyrene and poly(butyl methacrylate), and the third input vector corresponds to polyacrylic acid and poly(butyl methacrylate). Also in the function for calculating the regression parameter of the second-order term, an input vector and an output value have a one to-one relationship. In this example, the input vector is a composition of two feature vectors M and the output value is the regression parameter b. In one example, the calculation unit 12 inputs all combinations of input vectors into a machine learning model and calculates the regression parameter b for each combination. In the example of FIG. 5, the calculation unit 12 calculates a regression parameter $b_{12}$ corresponding to the combination of polystyrene and polyacrylic acid, a regression parameter $b_{13}$ corresponding to the combination of polystyrene and poly(butyl methacrylate), and a regression parameter $b_{23}$ corresponding to the combination of polyacrylic acid and poly(butyl methacrylate).

In step S14 shown in FIG. 5, the prediction unit 13 calculates a predicted value E by the following Scheffe polynomial (2) defined by six regression parameters $a_1$, $a_2$, $a_3$, $b_{12}$, $b_{13}$, and $b_{23}$. In the equation (2), the regression parameter a may be said to be a regression coefficient of the first-order term, and the regression parameter b may be said to be a regression coefficient of the second-order term. The variable r in the equation (2) means the combination ratio, which is the same as in the equation (1).

[Equation 2]

$$E = \sum_{1 \le i \le 3} a_i r_i + \sum_{1 \le i < j \le 3} b_{ij} r_i r_j \qquad (2)$$

Although three component objects are shown in FIGS. 4 and 5, the number of component objects is not limited and the information processing system 10 may process any number of component objects.

The information processing system 10 may output individual regression parameters based on the feature vectors of all related component objects, also for a regression model that includes third- or higher order terms or other parameters. In a case of calculating a regression parameter that does not depend on a specific explanatory variable, such as an intercept of linear regression, the information processing system 10 may output one regression parameter based on feature vectors of all component objects.

Although in the examples of FIGS. 4 and 5 the calculation unit 12 executes both the embedding function and interaction function, one of the two functions may be omitted. For example, the calculation unit 12 may calculate the regression parameter from the feature vector Z obtained by the machine learning model for the embedding function. In any case, the calculation unit 12 executes the machine learning to calculate the regression parameter.

In one example, the machine learning model for the embedding function, the machine learning model for the interaction function, the machine learning model for the regression parameter, and the regression model may be constructed by one neural network or may be constructed by a set of a plurality of neural networks. Alternatively, the machine learning model for the embedding function, the machine learning model for the interaction function, and the machine learning model for the regression parameter may be constructed by one neural network or may be constructed by a set of a plurality of neural networks.

[Program]

An information processing program for causing a computer or a computer system to function as the information processing system 10 includes a program code for causing the computer system to function as the acquisition unit 11, the calculation unit 12, and the prediction unit 13. The information processing program may be provided after being non-temporarily recorded on a tangible recording medium such as a CD-ROM, a DVD-ROM, or a semiconductor memory. Alternatively, the information processing program may be provided through a communication network as a data signal superimposed on a carrier wave. The provided information processing program is stored in, for example, the auxiliary storage unit 103. Each of the functional elements described above is realized by the processor 101 reading the information processing program from the auxiliary storage unit 103 and executing the information processing program.

[Effects]

As described above, an information processing system according to one aspect of the present disclosure includes at least one processor. The at least one processor is configured to: acquire a numerical representation and a combination ratio for each of a plurality of component objects; execute machine learning based on a plurality of the numerical representations to calculate a plurality of regression parameters corresponding to the plurality of component objects; and apply a plurality of the combination ratios to a regression model defined by the plurality of regression parameters to calculate a predicted value indicating characteristics of a composite object obtained by combining plurality of component objects.

An information processing method according to one aspect of the present disclosure is executed by an information processing system comprising at least one processor. The information processing method includes: acquiring a numerical representation and a combination ratio for each of a plurality of component objects; executing machine learning based on a plurality of the numerical representations to calculate a plurality of regression parameters corresponding to the plurality of component objects; and applying a plurality of the combination ratios to a regression model defined by the plurality of regression parameters to calculate a predicted value indicating characteristics of a composite object obtained by combining plurality of component objects.

An information processing program according to one aspect of the present disclosure causes a computer to execute: acquiring a numerical representation and a combination ratio for each of a plurality of component objects; executing machine learning based on a plurality of the numerical representations to calculate a plurality of regression parameters corresponding to the plurality of component objects; and applying a plurality of the combination ratios to a regression model defined by the plurality of regression parameters to calculate a predicted value indicating characteristics of a composite object obtained by combining plurality of component objects.

In such aspects, the machine learning is performed based on the data of each component object, and the plurality of regression parameters corresponding to the plurality of component objects are calculated. Then, the combination ratio is applied to the regression model defined by the regression parameters to predict the characteristics of the composite object. By utilizing the machine learning and regression model, it is possible to improve the accuracy of analysis of composite object even in a case where a sufficient amount of data cannot be prepared for the component objects.

Once the regression parameter is obtained, it is possible to change the combination ratio to instantaneously recalculate the characteristics of the composite object by the regression model. That is, the calculated regression parameter may be reused. By adopting a method of estimating the regression parameter by the machine learning, it is possible to execute processing of searching characteristics of the composite object rapidly while changing the combination ratio.

In the information processing system according to another aspect, the at least one processor may be configured to: input the plurality of numerical representations to a first machine learning model to calculate a plurality of feature vectors corresponding to the plurality of component objects; and input the plurality of feature vectors to a second machine learning model to calculate the plurality of regression parameters. By the series of procedures, even in a case where a sufficient amount of data cannot be prepared for the component objects, it is possible to further improve the accuracy of analysis of the composite object.

In the information processing system according to another aspect, the first machine learning model may include a machine learning model for an embedding function and a machine learning model for an interaction function. The at least one processor may be configured to: input the plurality of numerical representations to the machine learning model for the embedding function to calculate a plurality of first feature vectors corresponding to the plurality of component objects; input the plurality of first feature vectors into the machine learning model for the interaction function to calculate a plurality of second feature vectors corresponding to the plurality of component objects; and input the plurality of second feature vectors to the second machine learning model to calculate the plurality of regression parameters. By configuring the first machine learning model in this manner, even in a case where a sufficient amount of data cannot be prepared for the component objects, it is possible to further improve the accuracy of analysis of the composite object.

In the information processing system according to another aspect, the machine learning model for the embedding function may be a machine learning model that generates the first feature vector that is a fixed-length vector, from the numerical representation that is unstructured data. By using this machine learning model, the feature vector can be obtained from the numerical representation that cannot be represented by the fixed-length vector.

In the information processing system according to another aspect, the regression model may be a Scheffe polynomial. The at least one processor may be configured to calculate a plurality of regression coefficients of a first-order term of the Scheffe polynomial, as the plurality of regression parameters. By using the Scheffe polynomial that is often used in an issue related to blending, the composite object obtained by blending the plurality of component objects can be analyzed with high accuracy. In addition, a predicted value in which a degree of influence of a single component object is taken into consideration can be calculated by the regression coefficient of the first-order term.

In the information processing system according to another aspect, the at least one processor may be configured to further calculate a plurality of regression coefficients of a second-order term of the Scheffe polynomial, as the plurality of regression parameters. In this case, a predicted value in which a degree of influence of a synthesis of two component objects is further taken into consideration can be calculated by the regression coefficient of the second-order term.

In an information processing system according to another aspect, the component object may be a material, and the composite object may be a multi-component substance. In this case, even in a case where a sufficient amount of data cannot be prepared for the materials, it is possible to further improve the accuracy of analysis of the multi-component substance.

In the information processing system according to another aspect, the material may be a polymer or a monomer, and the multi-component substance may be a polymer alloy. In this case, even in a case where a sufficient amount of data cannot be prepared for the polymers or monomers, it is possible to further improve the accuracy of analysis of the polymer alloy. There are a huge variety of polymers or monomers, and correspondingly, there are a huge variety of polymer alloys. For such polymers, monomers, and polymer alloys, in general, only some of the possible combinations can be tested, and thus a sufficient amount of data cannot be obtained in many cases. According to this aspect, it is possible to accurately analyze the polymer alloy even in a case where the amount of data is not sufficient as described above.

[Modifications]

The present invention has been described in detail based on the embodiment. However, the present invention is not limited to the embodiment described above. The present invention can be modified in various ways without departing from its gist.

The processing procedure of the information processing method executed by at least one processor is not limited to the example in the embodiment described above. For example, some of the steps or processes described above may be omitted, or the steps may be executed in a different order. In addition, any two or more steps among the above-described steps may be combined, or a part of each step may be modified or deleted. Alternatively, other steps may be executed in addition to each of the above steps.

In a case of comparing the magnitudes of two numerical values in the information processing system, either of the two criteria of "equal to or greater than" and "greater than" may be used, or either of the two criteria of "equal to or less than" and "less than" may be used. Such criteria selection does not change the technical significance of the process of comparing the magnitudes of two numerical values.

In the present disclosure, the expression "at least one processor performs a first process, performs a second process, . . . , and performs an n-th process" or the expression corresponding thereto shows a concept including a case where a processor that executes n processes from the first process to the n-th process changes on the way. That is, this expression shows a concept including both a case where all of the n processes are performed by the same processor and a case where the processor is changed according to an any policy in the n processes.

REFERENCE SIGNS LIST

10: information processing system, 11: acquisition unit, 12: calculation unit, 13: prediction unit.

The invention claimed is:

1. An information processing system comprising at least one processor, wherein the at least one processor is configured to:

acquire a numerical representation and a combination ratio for each of a multiplicity of mutually different polymers or monomers, wherein the numerical representation represents attributes of the multiplicity of polymers or monomers, and wherein the combination ratio corresponds to a ratio among the multiplicity of polymers or monomers;

generate a first trained machine learning model by executing and repeating a first machine learning process comprising:

inputting a first input vector into a first untrained machine learning model to calculate a first output value;

calculating a first difference between the first output value and a first ground truth; and updating a first parameter of the first untrained machine learning model based on the first difference;

input a plurality of numerical representations to the first trained machine learning model to calculate a plurality of feature vectors corresponding to the multiplicity of polymers or monomers;

generate a second trained machine learning model by executing and repeating a second machine learning process comprising:

inputting a second input vector into a second untrained machine learning model to calculate a second output value;

calculating a second difference between the second output value and a second ground truth; and updating a second parameter of the second untrained machine learning model based on the second difference;

input the plurality of feature vectors to the second trained machine learning model to calculate a plurality of regression parameters corresponding to the multiplicity of polymers or monomers; and apply a plurality of the combination ratios to a regression model defined by the plurality of regression parameters to calculate a predicted value indicating characteristics of a polymer alloy obtained by combining the multiplicity of polymers or monomers;

change values of the plurality of combination ratios;

recalculate the predicted value indicating the characteristics of the polymer alloy, by using the changed values of the plurality of combination ratios and the calculated plurality of regression parameters;

output the calculated predicted value and the recalculated predicted value;

execute processing for searching for the characteristics of the polymer alloy using the calculated predicted value and the recalculated predicted value; and cause a display device to display a result of the processing for searching.

2. The information processing system according to claim 1, wherein the first machine learning model includes a machine learning model for an embedding function and a machine learning model for an interaction function, and wherein the at least one processor is configured to:

input the plurality of numerical representations to the machine learning model for the embedding function to calculate a plurality of first feature vectors corresponding to the multiplicity of polymers or monomers;

input the plurality of first feature vectors into the machine learning model for the interaction function to calculate a plurality of second feature vectors corresponding to the multiplicity of polymers or monomers; and input the plurality of second feature vectors to the second machine learning model to calculate the plurality of regression parameters.

3. The information processing system according to claim 2, wherein the machine learning model for the embedding function is a machine learning model that generates the first feature vector that is a fixed-length vector, from the numerical representation that is unstructured data.

4. The information processing system according to claim 1, wherein the regression model is a Scheffe polynomial, and wherein the at least one processor is configured to calculate a plurality of regression coefficients of a first-order term of the Scheffe polynomial, as the plurality of regression parameters.

5. The information processing system according to claim 4, wherein the at least one processor is configured to further calculate a plurality of regression coefficients of a second-order term of the Scheffe polynomial, as the plurality of regression parameters.

6. An information processing method executed by an information processing system comprising at least one processor, the method comprising:

acquiring a numerical representation and a combination ratio for each of a multiplicity of mutually different polymers or monomers, wherein the numerical representation represents attributes of the multiplicity of polymers or monomers, and wherein the combination ratio corresponds to a ratio among the multiplicity of polymers or monomers;

generating a first trained machine learning model by executing and repeating a first machine learning process comprising:

inputting a first input vector into a first untrained machine learning model to calculate a first output value;

calculating a first difference between the first output value and a first ground truth; and updating a first parameter of the first untrained machine learning model based on the first difference;

inputting a plurality of numerical representations to the first trained machine learning model to calculate a plurality of feature vectors corresponding to the multiplicity of polymers or monomers;

generating a second trained machine learning model by executing and repeating a second machine learning process comprising:

inputting a second input vector into a second untrained machine learning model to calculate a second output value;

calculating a second difference between the second output value and a second ground truth; and updating a second parameter of the second untrained machine learning model based on the second difference;

inputting the plurality of feature vectors to the second trained machine learning model to calculate a plurality of regression parameters corresponding to the multiplicity of polymers or monomers; and applying a plurality of the combination ratios to a regression model defined by the plurality of regression parameters to calculate a predicted value indicating characteristics of a polymer alloy obtained by combining the multiplicity of polymers or monomers;

changing values of the plurality of combination ratios;

recalculating the predicted value indicating the characteristics of the polymer alloy, by using the changed values of the plurality of combination ratios and the calculated plurality of regression parameters;

outputting the calculated predicted value and the recalculated predicted value;

executing processing for searching for the characteristics of the polymer alloy using the calculated predicted value and the recalculated predicted value; and cause a display device to display a result of the processing for searching.

7. A non-transitory computer-readable storage medium storing an information processing program for causing a computer to execute:

acquiring a numerical representation and a combination ratio for each of a multiplicity of mutually different polymers or monomers, wherein the numerical representation represents attributes of the multiplicity of polymers or monomers, and wherein the combination ratio corresponds to a ratio among the multiplicity of polymers or monomers;

generating a first trained machine learning model by executing and repeating a first machine learning process comprising:

inputting a first input vector into a first untrained machine learning model to calculate a first output value;

calculating a first difference between the first output value and a first ground truth; and updating a first parameter of the first untrained machine learning model based on the first difference;

inputting a plurality of numerical representations to the first trained machine learning model to calculate a plurality of feature vectors corresponding to the multiplicity of polymers or monomers;

generating a second trained machine learning model by executing and repeating a second machine learning process comprising:

inputting a second input vector into a second untrained machine learning model to calculate a second output value;

calculating a second difference between the second output value and a second ground truth; and updating a second parameter of the second untrained machine learning model based on the second difference;

inputting the plurality of feature vectors to the second trained machine learning model to calculate a plurality of regression parameters corresponding to the multiplicity of polymers or monomers; and applying a plurality of the combination ratios to a regression model defined by the plurality of regression parameters to calculate a predicted value indicating characteristics of a polymer alloy obtained by combining the multiplicity of polymers or monomers;

changing values of the plurality of combination ratios;

recalculating the predicted value indicating the characteristics of the polymer alloy, by using the changed values of the plurality of combination ratios and the calculated plurality of regression parameters;

outputting the calculated predicted value and the recalculated predicted value;

executing processing for searching for the characteristics of the polymer alloy using the calculated predicted value and the recalculated predicted value; and cause a display device to display a result of the processing for searching.

* * * * *